United States Patent
Wang et al.

(10) Patent No.: US 12,240,914 B2
(45) Date of Patent: Mar. 4, 2025

(54) ANTIBODY AGAINST FACTOR XIA IN ACTIVATED FORM OF COAGULANT FACTOR XI, PREPARATION METHOD THEREFOR AND USE THEREOF

(71) Applicant: MAB-LEGEND BIOTECH CO., LTD., Shanghai (CN)

(72) Inventors: Shaoxiong Wang, Shanghai (CN); Juehua Xu, Shanghai (CN); Yunhua Zhou, Shanghai (CN); Yongfeng Chen, Shanghai (CN)

(73) Assignee: MAB-LEGEND BIOTECH CO., LTD., Shanghai (CN)

( * ) Notice: Subject to any disclaimer, the term of this patent is extended or adjusted under 35 U.S.C. 154(b) by 596 days.

(21) Appl. No.: 17/423,426

(22) PCT Filed: Oct. 22, 2019

(86) PCT No.: PCT/CN2019/112412
§ 371 (c)(1),
(2) Date: Jul. 15, 2021

(87) PCT Pub. No.: WO2021/022676
PCT Pub. Date: Feb. 11, 2021

(65) Prior Publication Data
US 2022/0153872 A1    May 19, 2022

(30) Foreign Application Priority Data
Aug. 8, 2019  (CN) .......................... 201910729990.5

(51) Int. Cl.
| C07K 16/00 | (2006.01) |
| A61P 7/02  | (2006.01) |
| C07K 16/36 | (2006.01) |
| A61K 39/00 | (2006.01) |

(52) U.S. Cl.
CPC ............... *C07K 16/36* (2013.01); *A61P 7/02* (2018.01); *A61K 2039/505* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 2007/0224198 A1* | 9/2007 | Blackburn ............ C07K 16/40 424/145.1 |
| 2017/0355780 A1 | 12/2017 | Chen et al. |

FOREIGN PATENT DOCUMENTS

| CN | 104684932 A | 6/2015 |
| CN | 108409863 A | 8/2018 |
| CN | 109153726 A | 1/2019 |
| CN | 109476758 A | 3/2019 |
| EP | 3 581 587 A1 | 12/2019 |
| WO | 2013/167669 A1 | 11/2013 |
| WO | 2017/015619 A1 | 1/2017 |
| WO | 2017/127468 A1 | 7/2017 |
| WO | 2017/162791 A1 | 9/2017 |
| WO | 2017/218371 A1 | 12/2017 |
| WO | 2018/116267 A1 | 6/2018 |
| WO | 2018/116267 A2 | 6/2018 |

OTHER PUBLICATIONS

Notice of Reasons for Refusal, dated Jul. 11, 2022, issued in corresponding Japanese Patent Application No. 2021-541199.
David, Tovo et al., "Factor XIa-specific IgG and a reversal agent to probe factor XI function in thrombosis and hemostasis," Science Translational Medicine, vol. 8, No. 353, Aug. 2016, 353ra112, pp. 1-14.
Extended European Search Report, dated Jul. 26, 2022, issued in corresponding European Patent Application No. 19940544.0.
Al-Horani, Rami A. et al., "Factor XIa inhibitors: A review of the patent literature," Expert Opinion on Therapeutic Patents, vol. 26, No. 3, Feb. 2016, pp. 323-345.
International Search Report, dated May 14, 2020, issued in corresponding International Application No. PCT/CN2019/112412, filed Oct. 22, 2019.
First Search Report of CN Prior Application, issued in priority application CN Application No. 201910729990.5, filed Aug. 8, 2019.
Office Action, dated Feb. 3, 2020, issued in priority application CN Application No. 201910729990.5, filed Aug. 8, 2019.
Thomas, Dirk et al., "BAY 1213790, a fully human IgG1 antibody targeting coagulation factor XIa: First evaluation of safety, pharmacodynamics, and pharmacokinetics," Research and Practice in Thrombosis and Haemostasis, 2019, pp. 1-12.
Peng, Lifei, "FXI as a new target of antithrombotic therapy and its research progress," Chinese Journal of Pharmacology and Toxicology, vol. 25(Supple), p. 16, Sep. 2011. Abstract.

* cited by examiner

*Primary Examiner* — Meera Natarajan
(74) *Attorney, Agent, or Firm* — Kathleen D. Rigaut; Howson & Howson LLP

(57) ABSTRACT

Provided in the present application are an antibody against factor XIa in the activated form of coagulant factor XI, a preparation method therefor and the use thereof. The CDR of the heavy chain variable region of the antigen-binding fragment of the antibody comprises the amino acid sequence shown in SEQ ID NOs: 1-3, and the CDR of the light chain variable region thereof comprises the amino acid sequence shown in SEQ ID NOs: 4-6. The antibody can specifically bind to FXIa but not to FXI, and has the effect of inhibiting the endogenous pathway of human coagulation without affecting the exogenous pathway thereof, which can significantly inhibit the formation of arteriovenous shunt thrombosis, but does not increase the bleeding time and volume. Same has the potential to become an antithrombotic drug.

18 Claims, 11 Drawing Sheets

Specification includes a Sequence Listing.

ANTIBODY AGAINST FACTOR XIA IN ACTIVATED FORM OF COAGULANT FACTOR XI, PREPARATION METHOD THEREFOR AND USE THEREOF

CROSS REFERENCE TO RELATED APPLICATIONS

This application is a § 371 of International Application No, PCT/CN2019/112412, filed Oct. 22, 2019, which claims priority to Chinese Patent Application No. 201910729990.5 filed Aug. 8, 2019, the entire contents of each being incorporated by reference as though set forth in full.

INCORPORATION-BY-REFERENCE OF MATERIAL SUBMITTED IN ELECTRONIC FORM

Applicant hereby incorporates by reference the Sequence Listing material filed in electronic form herewith. This file is labeled "SEQLIST.txt", dated Jul. 15, 2021 and is 6,156 bytes in size.

TECHNICAL FIELD

The present application belongs to the field of biotechnology, relates to an antibody and a preparation method and application thereof and, in particular, to an anti-Factor XIa antibody and a preparation and use thereof, wherein Factor XIa is the activated form of coagulation factor XI.

BACKGROUND

Blood coagulation is a complex process and is roughly divided into three stages: formation of prothrombin activator, conversion of prothrombin to thrombin, and conversion of fibrinogen to fibrin. There are two different mechanisms for the formation of prothrombin activator, namely the intrinsic pathway and the extrinsic pathway, respectively. These two types of mechanisms are combined in the formation of thrombin and the formation of fibrin, both of which are also called the common pathway. The coagulation reaction amplifies coagulation signals cascade by cascade by employing a cascade mechanism, and the biochemical essence of such the reaction is a series of enzymatic reactions of blood coagulation factors in plasma, in which upstream factors activate their downstream factors and soluble fibrinogen (FI) is ultimately converted into insoluble fibrin (FIa).

The activated form of coagulation-factor XI, Factor XIa (FXIa), is thrombin generated by shearing zymogen coagulation factor XI (Factor XI, FXI), and is involved in the intrinsic coagulation pathway. The human FXI gene is located on chromosome NO. 4 (4q32-35), is 23 kb in length, and includes 15 exons. The human FXI protein has a molecular weight of 160 kD and is homodimeric in the structure; and each subunit consists of 607 amino acids and includes one heavy chain and one light chain, of which the heavy chain includes four Apple domains (A domains) and the light chain is mainly the enzyme activity region. The FXI protein in the human body is mainly synthesized by hepatocytes, the concentration of FXI in plasma is about 5 μg/mL, and its half-life is about 52 hours. In the coagulation pathway, FXI can be activated by the activated coagulation factor FXII (FXIIa) and thrombin to generate FXIa and then further activate FIX and downstream coagulation reactions.

The population with FXI deficiency usually do not suffer from spontaneous bleeding or have no or only a very slight tendency to bleed. The latest epidemiological studies have shown that the FXI deficiency is negatively associated with the risk of death due to cerebral ischemic stroke. Among the population with the FXI deficiency, the incidence of ischemic stroke caused by thrombus is significantly lower than that among the normal population. Among the population with a high FXI expression level, the incidence of venous thrombus is high than that among the normal population. In a phase II clinical trial of FXI antisense oligonucleotide, 200 mg of FXI antisense oligonucleotide can significantly reduce the incidence of deep venous thrombus among patients undergoing knee replacement surgery, without increasing the risk of bleeding among the subject population. It can be seen that FXI and the intrinsic coagulation pathway involving FXI may play an important role in the formation of thrombus in the human body under pathological conditions. Therefore, FXI, especially its activated form FXIa, is an ideal target for antithrombotic therapy.

CN104684932A discloses antibodies capable of binding to the coagulation factor XI and/or its activated form Factor XIa and use thereof. The monoclonal antibodies are capable of inhibiting platelet aggregation and by this inhibiting thrombus without compromising hemostasis, but the monoclonal antibodies have a binding effect on both FXI and FXIa.

CN107922505A discloses coagulation factor XI antibodies and methods of use. The antibodies bind to the catalytic domain of FXI and/or FXIa, but do not have the function of specifically binding to either FXI or FXIa.

Therefore, in the existing art, the coagulation factor XI antibody has a binding effect on both FXI and FXIa, but has no specific binding function on FXIa. Since FXIa is a more ideal target for antithrombotic treatment than FXI, screening and obtaining antibodies that can specifically bind to FXIa is of great significance in the field of pathological thrombus treatment.

SUMMARY

In view of deficiencies in the existing art, the present application provides an anti-Factor XIa antibody and a preparation and use thereof, wherein Factor XIa is the activated form of coagulation factor XI. The antibody can specifically bind to FXIa but not to FXI, and thus has the potential to become antithrombotic drugs.

To achieve this object, the present application adopts solutions below.

In a first aspect, the present application provides an antigen-binding fragment, wherein CDRs of the heavy chain variable region of the antigen-binding fragment include amino acid sequences as set forth in SEQ ID NOs: 1 to 3; and CDRs of the light chain variable region of the antigen-binding fragment include amino acid sequences as set forth in SEQ ID NOs: 4 to 6, wherein the amino acid sequence as set forth in SEQ ID NO: 1 is ELSMH;

the amino acid sequence as set forth in SEQ ID NO: 2 is GFDPEDGETIYAQKFQG;

the amino acid sequence as set forth in SEQ ID NO: 3 is DRPVRGVIPYYYYYGMDV;

the amino acid sequence as set forth in SEQ ID NO: 4 is SGSRSNIGSRPVN;

the amino acid sequence as set forth in SEQ ID NO: 5 is IDHQRPS; and the amino acid sequence as set forth in SEQ ID NO: 6 is AAWDDSLDAYV.

Preferably, CDRs of the heavy chain variable region of the antigen-binding fragment include nucleic acid sequences as set forth in SEQ ID NOs: 7 to 9; wherein the nucleic acid sequence as set forth in SEQ ID NO: 7 is GAATTATCCATGCAC;

the nucleic acid sequence as set forth in SEQ ID NO: 8 is as follows:

GGTTTTGATCCTGAAGATGGTGAAACA

ATCTACGCACAGAAGTTCCAGGGC;

and the nucleic acid sequence as set forth in SEQ ID NO: 9 is as follows:

GATCGGCCGGTTCGGGGAGTTATTCCTT

ACTACTACTACTACGGTATGGACGTC.

Preferably, CDRs of the light chain variable region of the antigen-binding fragment include nucleic acid sequences as set forth in SEQ ID NOs: 10 to 12; wherein the nucleic acid sequence as set forth in SEQ ID NO: 10 is as follows:

TCTGGAAGCCGCTCCAACATCGGAAGTA

GGCCTGTAAAC;

the nucleic acid sequence as set forth in SEQ ID NO: 11 is ATTGATCATCAGCGGCCCTCA; and the nucleic acid sequence as set forth in SEQ ID NO: 12 is as follows:

GCAGCATGGGATGACAGCCTGGATGCTT

ATGTC.

Preferably, the heavy chain variable region of the antigen-binding fragment includes an amino acid sequence as set forth in SEQ ID NO: 13. wherein the amino acid sequence as set forth in SEQ ID NO: 13 is as follows:

QVQLVQSGAEVKKPGASVKVSCKVSGYTLTELSMH

WVRQAPGKGLEWMGGFDPEDGETIYAQKFQGRVTM

TEDTSTDTAYMELSSLRSEDTAVYYCATDRPVRGV

IPYYYYYGMDVWGQGTLVTVSS.

Preferably, the light chain variable region of the antigen-binding fragment includes an amino acid sequence as set forth in SEQ ID NO: 14; wherein the amino acid sequence as set forth in SEQ ID NO: 14 is as follows:

QSALTQPPSASGTPGQTVTISCSGSRSNIGSRPVN

WYQHLPGTAPKLLIYIDHQRPSGVPDRFSGSKSGT

SASLAISGLQSDDEADYYCAAWDDSLDAYVFGTGT

KVTVL.

Preferably, the heavy chain variable region of the antigen-binding fragment includes an nucleic acid sequence as set forth in SEQ ID NO: 15; wherein the nucleic acid sequence as set forth in SEQ ID NO: 15 is as follows:

CAGGTCCAGCTGGTACAGTCTGGGGCTGAGGTGAA

GAAGCCTGGGGCCTCAGTGAAGGTCTCCTGCAAGG

TTTCCGGATACACCCTCACTGAATTATCCATGCAC

TGGGTGCGACAGGCTCCTGGAAAAGGGCTTGAGTG

GATGGGAGGTTTTGATCCTGAAGATGGTGAAACAA

TCTACGCACAGAAGTTCCAGGGCAGAGTCACCATG

ACCGAGGACACATCTACAGACACAGCCTACATGGA

GCTGAGCAGCCTGAGATCTGAGGACACGGCCGTGT

ATTACTGTGCAACAGATCGGCCGGTTCGGGGAGTT

ATTCCTTACTACTACTACGGTATGGACGTCTG

GGGCCAAGGGACCCTGGTCACCGTCTCGAGC.

Preferably, the light chain variable region of the antigen-binding fragment includes an nucleic acid sequence as set forth in SEQ ID NO: 16; wherein the nucleic acid sequence as set forth in SEQ ID NO: 16 is as follows:

CAGTCTGCCCTGACTCAGCCACCCTCAGCGTCTGG

GACCCCCGGGCAGACGGTCACCATCTCTTGCTCTG

GAAGCCGCTCCAACATCGGAAGTAGGCCTGTAAAC

TGGTACCAGCACCTCCCAGGAACGGCCCCCAAACT

CCTCATCTATATTGATCATCAGCGGCCCTCAGGGG

TCCCTGACCGATTCTCTGGCTCCAAGTCTGGCACC

TCAGCCTCCCTGGCCATCAGTGGGCTCCAGTCTGA

CGATGAGGCTGATTATTACTGTGCAGCATGGGATG

ACAGCCTGGATGCTTATGTCTTCGGAACTGGGACC

AAGGTCACCGTCCTA.

In a second aspect, the present application provides an anti-Factor XIa antibody that includes the antigen-binding fragment described in the first aspect, wherein Factor XIa is the activated form of coagulation factor XI.

Preferably, the antibody further includes any one or a combination of at least two of a human IgG1 constant region, a human IgG2 constant region, a human IgG3 constant region, or a human IgG4 constant region, preferably the human IgG1 constant region.

According to the present application, the concentrations of FXI and FXIa in human plasma are about 5 μg/mL (30 nM) and 0.6 ng/mL (4 pM), respectively; the half-life of FXI in the human body is about 52 hours; and, the newly synthesized FXI by the liver can reach about 16 mg per day. Form the above, it can be seen that the concentration of FXI in the human body is much higher than the concentration of FXIa. Therefore, compared with antibodies that bind to both FXIa and FXI, screening for antibodies that bind only to FXIa but not to FXI can significantly reduce the amount of medication administered in the clinical application. In addition, antibodies that bind only to FXIa are clinically safer than antibodies that bind to both FXIa and FXI.

In the present application, the antibody, which can strongly bind to FXIa but does not bind to FXI, is capable of increasing activated partial thromboplastin time (aPTT), has no significant effect on prothrombin time (PT), and has the effect of inhibiting the intrinsic pathway of human coagulation without affecting the extrinsic pathway.

In a third aspect, the present application provides a nucleic acid molecule that includes a DNA fragment encoding the antigen-binding fragment described in the first aspect and/or the antibody described in the second aspect.

In a fourth aspect, the present application provides an expression vector that includes the nucleic acid molecule described in the third aspect.

Preferably, the expression vector includes a pcDNA3.3 expression vector.

In a fifth aspect, the present application provides a host cell that is transfected with the nucleic acid molecule described in the third aspect and/or the expression vector described in the fourth aspect.

Preferably, the host cell includes a mammalian cell, preferably a Chinese hamster ovary cell.

In a sixth aspect, the present application provides a preparation method of the antigen-binding fragment described in the first aspect and/or the antibody described in the second aspect, including the following steps:

(1) ligating DNA fragments of a heavy chain variable region and a light chain variable region of an antibody into an expression vector, transferring the expression vector into a competent cell, culturing, and selecting a monoclonal cell for screening; and (2) transferring the screened expression vector into a host cell, culturing, collecting a supernatant, and performing separation and purification to obtain the antibody.

In a seventh aspect, the present application provides a pharmaceutical composition that includes any one or a combination of at least two of the antigen-binding fragment described in the first aspect, the antibody described in the second aspect, the nucleic acid molecule described in the third aspect, the expression vector described in the fourth aspect, or the host cell described in the fifth aspect.

Preferably, the pharmaceutical composition further includes any one or a combination of at least two of a pharmaceutically acceptable carrier, excipient, or diluent.

In an eighth aspect, the present application provides a therapeutic agent that is ligated to any one or a combination of at least two of the antigen-binding fragment described in the first aspect, the antibody described in the second aspect, the nucleic acid molecule described in the third aspect, the expression vector described in the fourth aspect, the host cell described in the fifth aspect, or the pharmaceutical composition described in the seventh aspect.

Preferably, the therapeutic agent further includes any one or a combination of at least two of a pharmaceutically acceptable carrier, excipient, or diluent.

In a ninth aspect, the present application provides use of the antigen-binding fragment described in the first aspect, the antibody described in the second aspect, the nucleic acid molecule described in the third aspect, the expression vector described in the fourth aspect, the host cell described in the fifth aspect, or the therapeutic agent described in the ninth aspect in the preparation of antithrombotic drugs.

Compared with the existing art, the present application has beneficial effects described below.

(1) The 14624 monoclonal antibody in the present application strongly binds to FXIa with a EC50 of 0.056 nM, but does not bind to FXI. The 14624 monoclonal antibody has a high affinity with FXIa, and its $K_D$ is 2.314E-11 M.

(2) The 14624 monoclonal antibody in the present application increases the aPTT without any significant effect on the PT, and has the effect of inhibiting the intrinsic pathway of human coagulation without affecting the extrinsic pathway.

(3) The 14624 monoclonal antibody in the present application has a significant inhibitory effect on FXIa-mediated conversion of FIX to its activated form FIXa, and is capable of inhibiting the FXI-mediated generation of FIXa.

(4) The 14624 monoclonal antibody in the present application has the specific inhibitory effect on FXIa, and does not specifically bind to other coagulation factors in the intrinsic and extrinsic coagulation pathways.

(5) The 14624 monoclonal antibody in the present application significantly inhibits the formation of arteriovenous shunt thrombus without increasing bleeding time or bleeding amount, and significantly increases the aPTT without affecting the PT and the platelet count.

(6) The 14624 monoclonal antibody in the present application has the potential to become antithrombotic drugs.

DETAILED DESCRIPTION

To further elaborate on the technical means adopted and the effects achieved in the present application, the present application is described below in conjunction with the examples and drawings. It is to be understood that the specific examples set forth below are intended to illustrate but not to limit the present application.

Experiments without specific techniques or conditions noted in the examples are conducted according to techniques or conditions described in the literature in the art or a product specification. The reagents or instruments used herein without manufacturers specified are conventional products commercially available from proper channels.

EXAMPLE 1 SCREENING AND CONSTRUCTION OF ANTIBODY MOLECULES

The antigens FXIa and FXI screened from the human natural phage Fab library (Enzyme Research Laboratories) were labeled with biotin using a labelling kit, i.e., an EZ-Link Sulfo-NHS-LC-Biotinylation kit (Thermo Scientific, Cat. No.: 21435), and desalted using a Zeba desalting column (Thermo Scientific, Cat. NO.: 89891).

The strategy for screening antibodies was as follows: Fab fragments that bound to FXIa but not to FXI were selected. 20 unique sequences were obtained after screening and sequencing. Sequences of the heavy chain variable region and the light chain variable region were amplified by PCR, respectively. The amplified sequences were inserted into a pcDNA3.3 expression vector. CHO cells were transfected with the expression vector. The supernatant secreted by cultured cells was purified to obtain a full-length IgG1 monoclonal antibody 14624. The sequence information of the monoclonal antibody 14624 is shown in SEQ ID NOs: 1 to 16.

Clone 076D-M007-H04-CDRL3-N110D light and heavy chain variable region sequences obtained from Bayer's U.S. Pat. No. 9,783,614B2 were used as the positive control. After the light and heavy chain variable region sequences were synthesized, the sequences were inserted into a pcDNA3.3 expression vector, CHO cells were transfected, and the supernatant secreted by cultured cells was purified to obtain a full-length IgG1 monoclonal antibody N110D as the positive control antibody.

EXAMPLE 2 VALIDATION OF THE SPECIFIC FUNCTION OF THE ANTI-HUMAN FXIa FULL-LENGTH HUMAN MONOCLONAL ANTIBODY 14624

The binding potency of the anti-human FXIa full-length human monoclonal antibody 14624 to the coagulation factor FXIa or FXI was detected by ELISA.

Figure 1A:
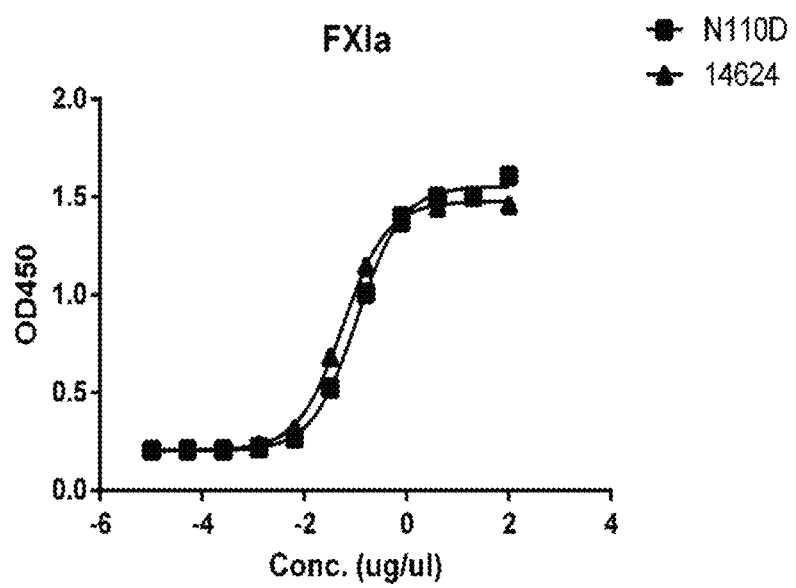
FIG. 1(A) illustrates a curve of the monoclonal antibody 14624 binding to the antigen human FXIa.
Figure 1B:
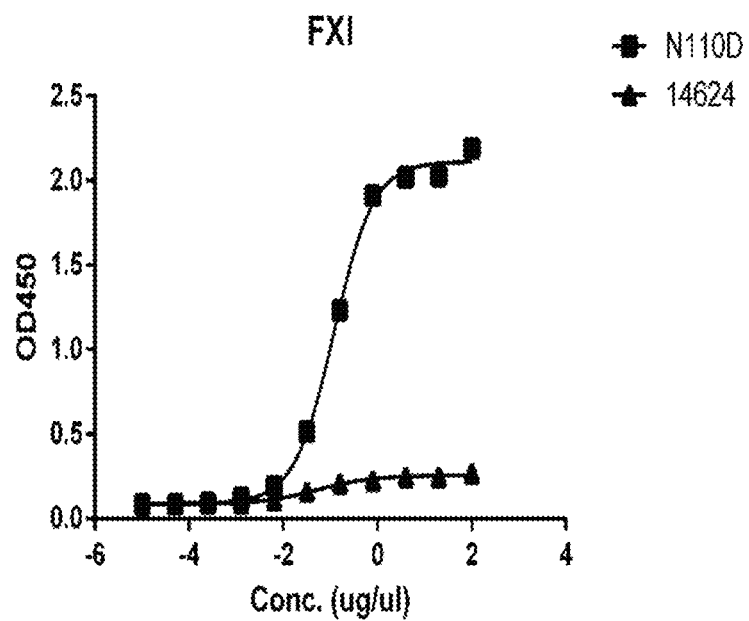
FIG. 1(B) illustrates a curve of the monoclonal antibody 14624 binding to FXI.

Results are shown in FIG. 1(A) and Table 1. The monoclonal antibody 14624 of the present application bound strongly to FXIa, and its EC50 was 0.056 nM, which was equivalent to the EC50 of the positive control antibody N110D. As shown in FIG. 1(B), the monoclonal antibody 14624 of the present application did not bind to FXI.

TABLE 1

| Antibody type | EC50 (FXIa, nM) |
| --- | --- |
| 14624 | 0.056 |
| N110D | 0.11 |

EXAMPLE 3 DETERMINATION OF THE ANTICOAGULANT ACTIVITY OF ANTIBODIES IN HUMAN PLASMA BY ACTIVATED PARTIAL THROMBOPLASTIN TIME (aPTT) AND PROTHROMBIN TIME (PT)

The aPTT was used for detecting the activity of coagulation factors in intrinsic and common pathways, and the PT was used for detecting the activity of coagulation factors in extrinsic and common pathways. Specific steps are as follows.

90 μL of standard human plasma (Dade Behring Diagnostics, Co., Ltd.) was mixed with 10 of antibodies to be detected at various concentrations (0 to 8 μM), respectively, and the mixtures were incubated for 5 min and then detected and analyzed on a CA-600 automatic coagulometer (Sysmex Ltd.) using aPTT kits and PT kits (Dade Behring Diagnostics, Co., Ltd.).

Figure 2A:
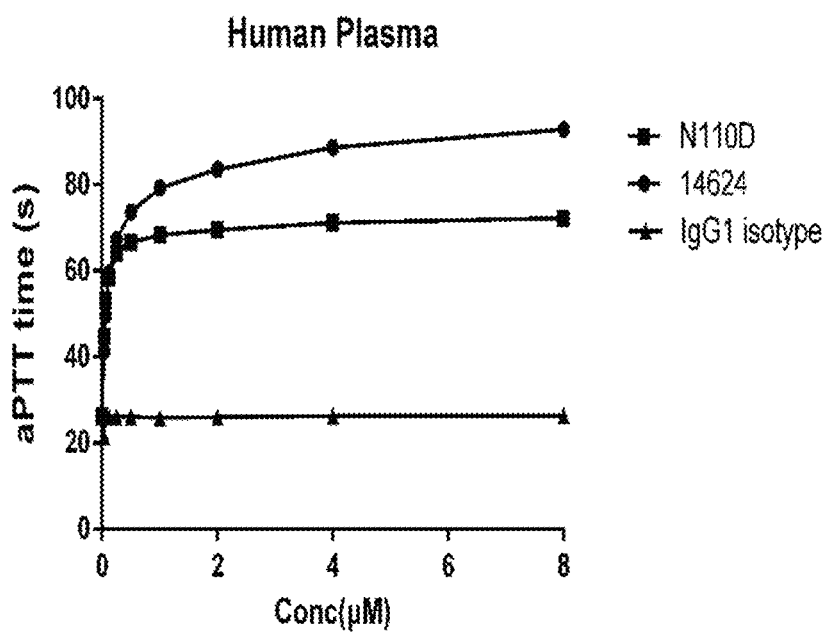
FIG. 2(A) illustrates the effect of the monoclonal antibody 14624 on activated partial thromboplastin time (aPTT) in human plasma.
Figure 2B:
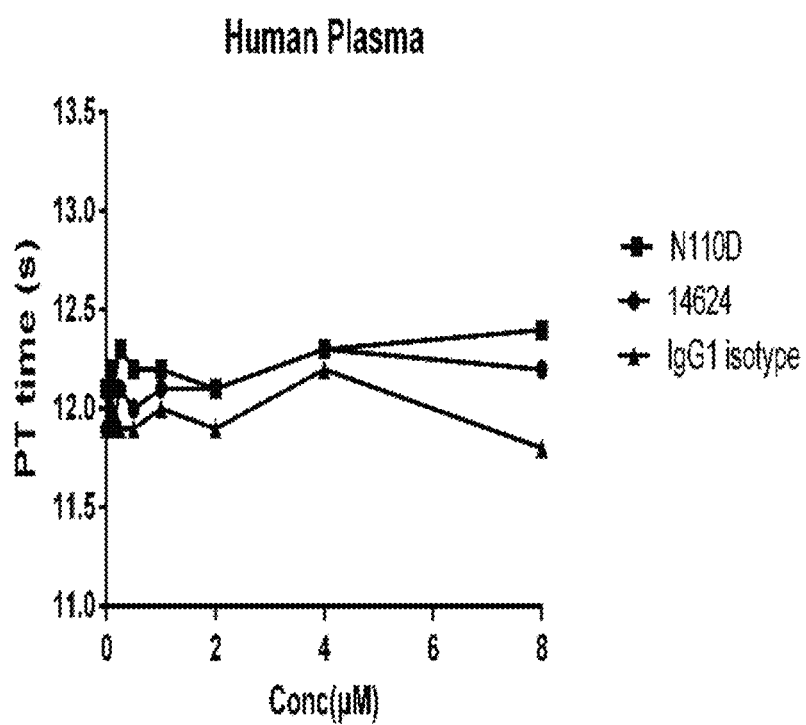
FIG. 2(B) illustrates the effect of the monoclonal antibody 14624 on prothrombin time (PT) in human plasma.

As shown in FIGS. 2(A) and 2(B), the monoclonal antibody 14624 of the present application can increase the activated partial thromboplastin time (aPTT), and showed certain concentration dependence in the low concentration range; however, it had no significant effect on the prothrombin time (PT), which indicated that the monoclonal antibody 14624 can inhibit the intrinsic pathway of human coagulation without affecting the extrinsic pathway.

EXAMPLE 4 DETECTION OF THE ANTICOAGULANT ACTIVITY OF ANTIBODIES IN NON-HUMAN PLASMA BY ACTIVATED PARTIAL THROMBOPLASTIN TIME (aPTT) AND PROTHROMBIN TIME (PT)

The anticoagulant activity of the monoclonal antibody 14624 in cynomolgus monkey plasma (cyno plasma) and New Zealand white rabbit plasma (rabbit plasma) was detected according to the method in Example 3.

Figure 3A:
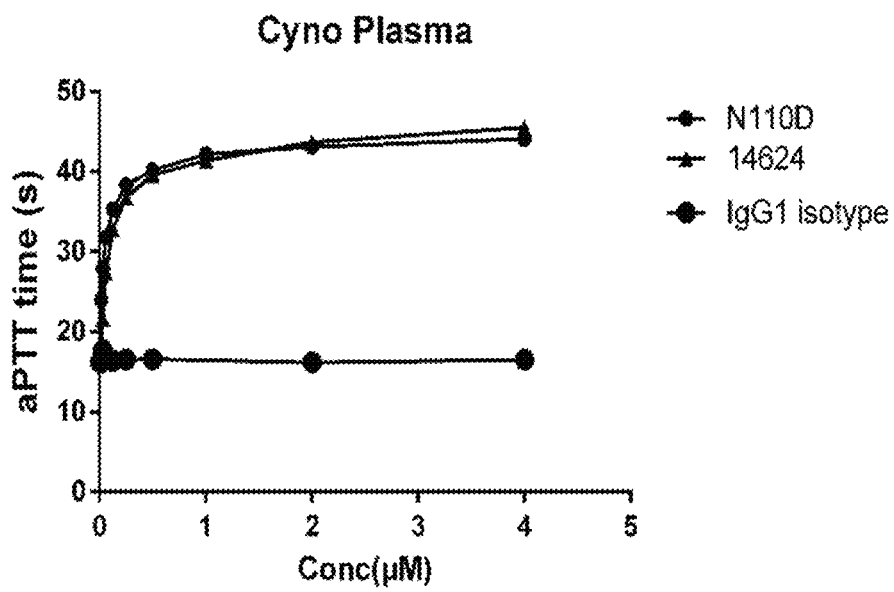
FIG. 3(A) illustrates the effect of the monoclonal antibody 14624 on activated partial thromboplastin time (aPTT) in cynomolgus monkey plasma.
Figure 3B:
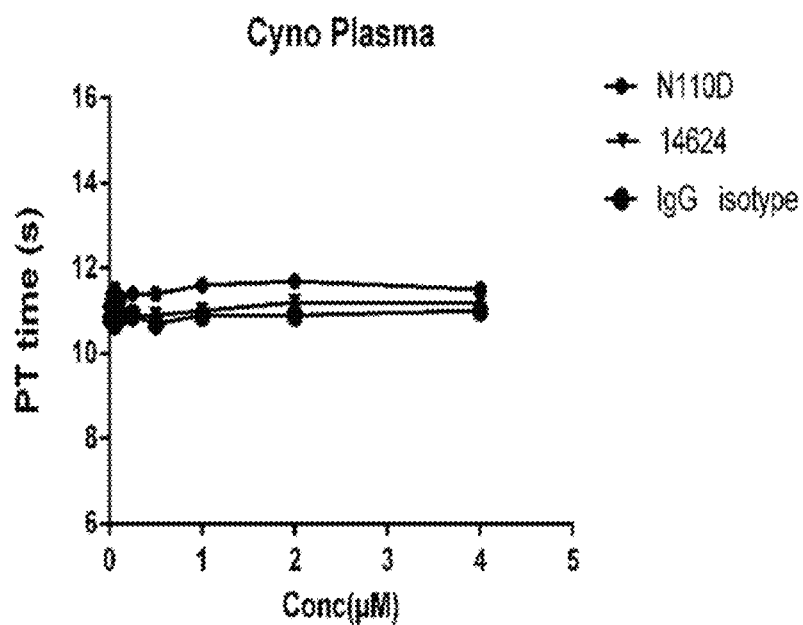
FIG. 3(B) illustrates the effect of the monoclonal antibody 14624 on prothrombin time (PT) in cynomolgus monkey plasma.
Figure 4A:
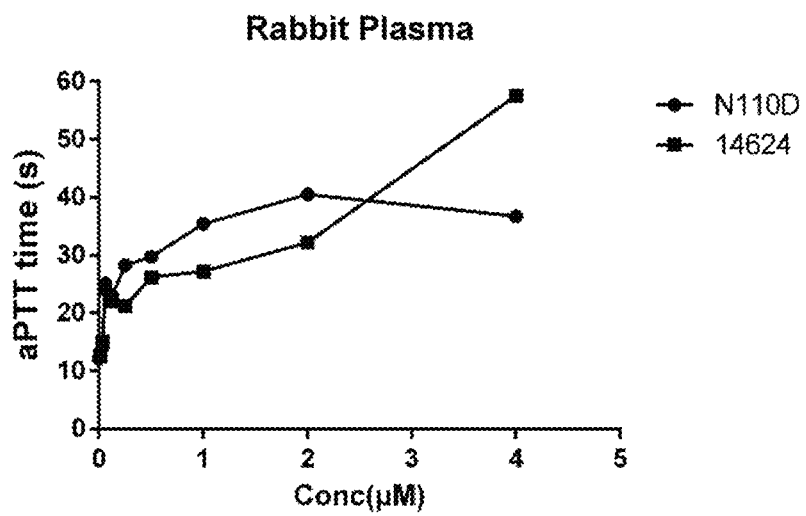
FIG. 4(A) illustrates the effect of the monoclonal antibody 14624 on activated partial thromboplastin time (aPTT) in New Zealand white rabbit plasma.
Figure 4B:
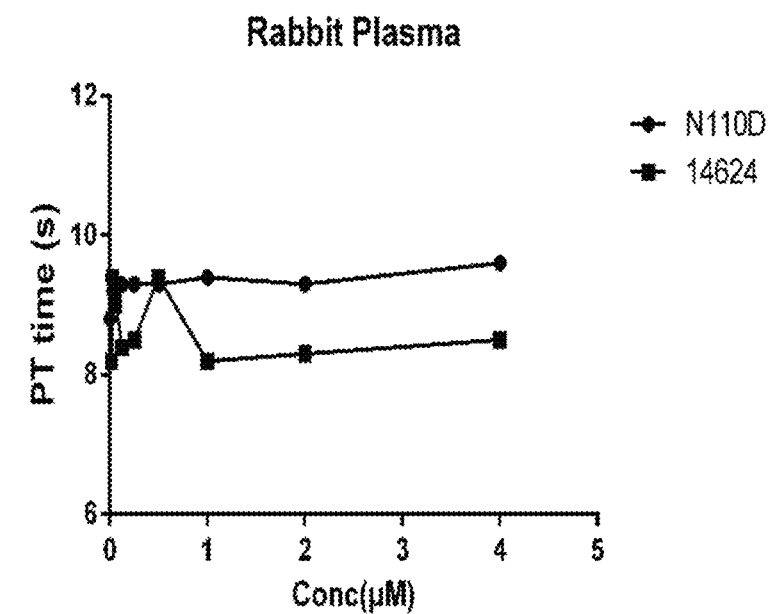
FIG. 4(B) illustrates the effect of the monoclonal antibody 14624 on prothrombin time (PT) in New Zealand white rabbit plasma.

As shown in FIGS. 3(A) and 3(B), the monoclonal antibody 14624 can increase the activated partial thromboplastin time (aPTT) in cyno plasma, and showed certain concentration dependence in the low concentration range; however, it had no significant effect on the prothrombin time (PT). As shown in FIGS. 4(A) and 4(B), the monoclonal antibody 14624 can increase the activated partial thromboplastin time (aPTT) in rabbit plasma, and showed certain concentration dependence in the low concentration range; however, it had no significant effect on the prothrombin time (PT). It indicated that the monoclonal antibody 14624 had the cross reaction with FXIa in cynomolgus monkeys and New Zealand white rabbits. Concentration values required for doubling aPTT in plasma of human, cynomolgus monkeys and New Zealand white rabbits are shown in Table 2.

TABLE 2

Antibody concentration values required for doubling aPTT in human, cynomolgus monkeys and New Zealand white rabbits

| Antibody type | 2 × aPTT Human plasma (μM) | 2 × aPTT Cyno plasma (μM) | 2 × aPTT Rabbit plasma (μM) |
|---|---|---|---|
| 14624 | 0.0625~0.125 | 0.125 | 0.0625~0.125 |
| N110D | 0.0625 | 0.0625 | <0.0625 |

EXAMPLE 5 DETECTION OF THE AFFINITY BETWEEN THE ANTI-FXIa ANTIBODY WITH HUMAN FXIa

In this example, the affinity between FXIa and the monoclonal antibody 14624 was quantitatively detected in real time using BIAcore T200 in a surface plasmon resonance (SPR) detection manner to evaluate the association-dissociation kinetics of the anti-FXIa antibody and FXIa. Specific steps are as follows.

(1) Antibody capture: The antibody to be detected was diluted to 1 μg/mL using 1×PBS buffer, and captured on Protein A chip at a flow rate of 10 μL/min for 15 s. The N110D antibody and the 14624 antibody were captured to Fc2 and Fc4 channels respectively.

(2) Sample testing conditions: The binding characteristics of FXIa and antibodies were preliminarily determined and evaluated in a manual mode. 10 nM was determined as the maximum analytical concentration of FXIa. A total of 10 concentrations for analysis were set by a 2-fold serial dilution: 0 nM, 0.01953 nM, 0.039625 nM, 0.078125 nM, 0.15625 nM, 0.3125 nM, 0.625 nM, 1.25 nM, 2.5 nM, 5 nM, and 10 nM. During the sample analysis, the flow rate was set to be 30 μL/min, the binding time was 120 s, and the dissociation time was 600 s.

(3) Regeneration conditions: With reference to other experiments, preliminary determination and evaluation were performed in a manual mode. Gly-HCl buffer (pH=1.5) was used as the regeneration buffer when the binding affinity between the antibody to be detected and FXIa was analyzed using Protein A chip. During the regeneration, the flow rate was set to be 30 μL/min, and the regeneration time was 30 s.

(4) Kinetic parameter determination: The experiment was carried out in a multi-cycle mode, in which the response signal took the analysis time as the horizontal coordinate and the response value as the vertical coordinate. The obtained data were fitted by BIAcore T200 analysis software, during which a 1:1 Langmuir binding model was used as a fitting model, so as to determine the kinetic constants such as an association rate constant, a dissociation rate constant, and an association-dissociation constant.

Figure 5A:
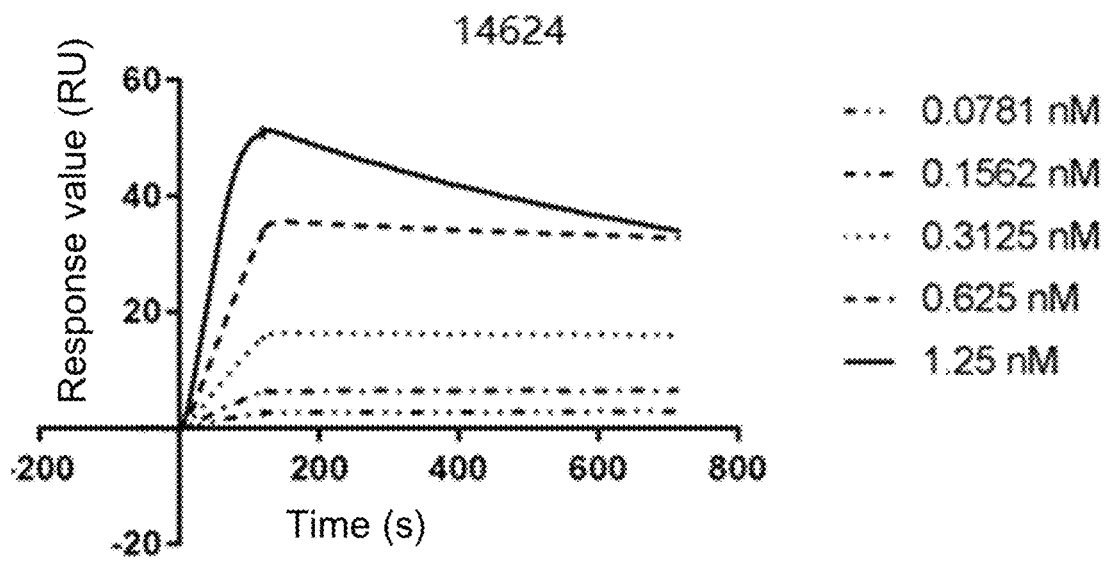
FIG. 5(A) illustrates a multi-cycle kinetics testing curve of FXIa and the 14624 antibody.
Figure 5B:
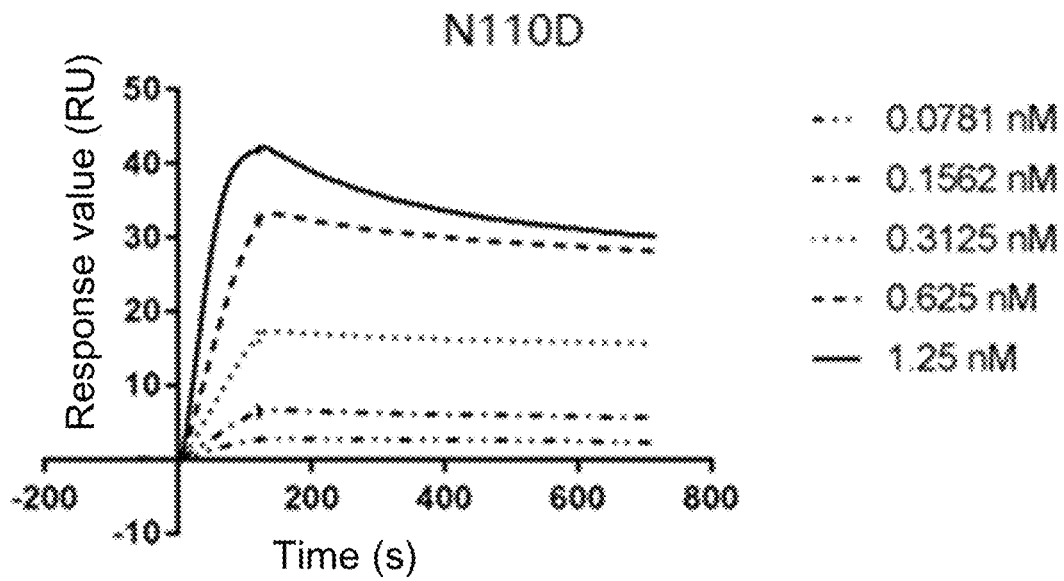
FIG. 5(B) illustrates a multi-cycle kinetics testing curve of FXIa and the N110D antibody.

The SPR spectra of the binding of the immobilized antibodies 14624 and N110D to FXIa are shown in FIGS. 5(A) and 5(B), and it can be seen that the response of the antibodies was gradually increased as the concentration of FXIa was gradually increased. Table 3 shows the association-dissociation constants (KD) of the antibodies for FXIa. Since KD≤$10^{-7}$ M is considered to a high affinity, the antibodies N110D and 14624 both had a high affinity with FXIa.

TABLE 3

| Antibody type | $k_{on}$ (1/Ms) | $k_{dis}$ (1/s) | $K_D$ (M) |
|---|---|---|---|
| 14624 | 1.059E+8 | 0.002451 | 2.314E−11 |
| N110D | 1.542E+8 | 0.001889 | 1.225E−11 |

EXAMPLE 6 FUNCTIONAL NEUTRALIZATION OF THE ANTIBODY ON FXIa

In this example, the activity of human FXIa was determined by digesting a specific chemical substrate, S-2366 (Diapharma Inc.), with FXIa and continuously monitoring the absorbance changes of enzyme-digested products using a microplate reader. In order to detect the inhibitory activity of anti-FXIa antibodies, FXIa was diluted to a final concentration of 2.5 nM with buffer (50 mM HEPES (pH=7.4), 145 mM NaCl, 5 mM KCl, 0.1% PEG8000, and 0.1% BSA), and incubated with antibodies at various concentrations for 5 min at room temperature, and then S-2366 was added to the antigen-antibody mixtures to make the final concentration reach 4 mM. The changes of absorbance at 405 nm were immediately monitored using a SpetraMax 190 microplate reader (Molecular Devices Inc.) in the kinetic-measurement mode for 30 min at 15 s intervals, and the obtained data were analyzed using the GraphPad Prism software.

Figure 6:
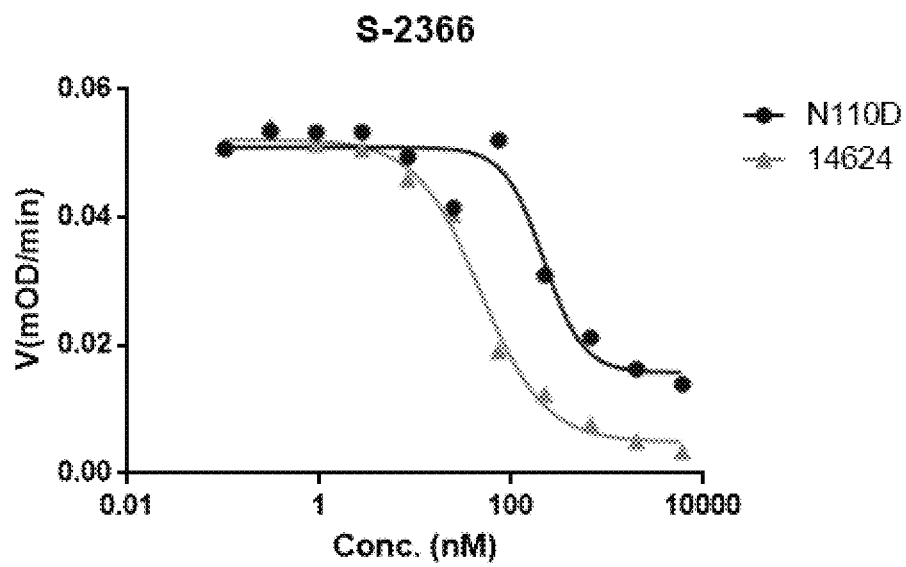
FIG. 6 illustrates a concentration-response curve of the inhibition of the human FXIa from hydrolyzing S-2366 by the monoclonal antibody 14624.

Results are shown in FIG. 6 and Table 4. In FIG. 6, the logs of antibody concentrations were taken as horizontal coordinates, and the rates of enzyme reaction were taken as vertical coordinates. Using Graphpad Prism software, four-parameter equation was used to fit the curves to obtain the IC50 values. IC50 indicates the concentration of the antibody for 50% inhibition of the enzyme reaction rate, and the smaller the IC50 value, the stronger the inhibitory activity of the antibody. The antibody 14624 showed a stronger ability to inhibit the enzyme activity of FXIa than N110D.

TABLE 4

| Antibody type | IC50 (nM) |
|---|---|
| 14624 | 47.32 |
| N110D | 217.1 |

EXAMPLE 7 INHIBITORY EFFECT OF THE ANTIBODY ON THE CONVERSION OF FIX TO ITS ACTIVATED FORM FIXa MEDIATED BY FXIa

The human FIX at the final concentration of 200 nM, the human FXIa at the final concentration of 5 nM, and 1 μM of the antibody to be detected were incubated in a buffer (50 mM HEPES (pH=7.4), 145 mM NaCl, 5 mM KCl, 5 mM $CaCl_2$, 0.1% PEG 8000, and 0.1% BSA) at room temperature. The reaction in 50 μL of the reaction solution was terminated using loading buffer of SDS-PAGE after 0, 15, 30, 45, and 60 min. The samples were separated by 10% non-reducing SDS-PAGE electrophoresis and then transferred to the PVDF membrane. The expression levels of FIX and FIXa were detected by Western blotting using the murine anti-human FIX IgG (Haematologic Technologies, Inc.).

Figure 7:
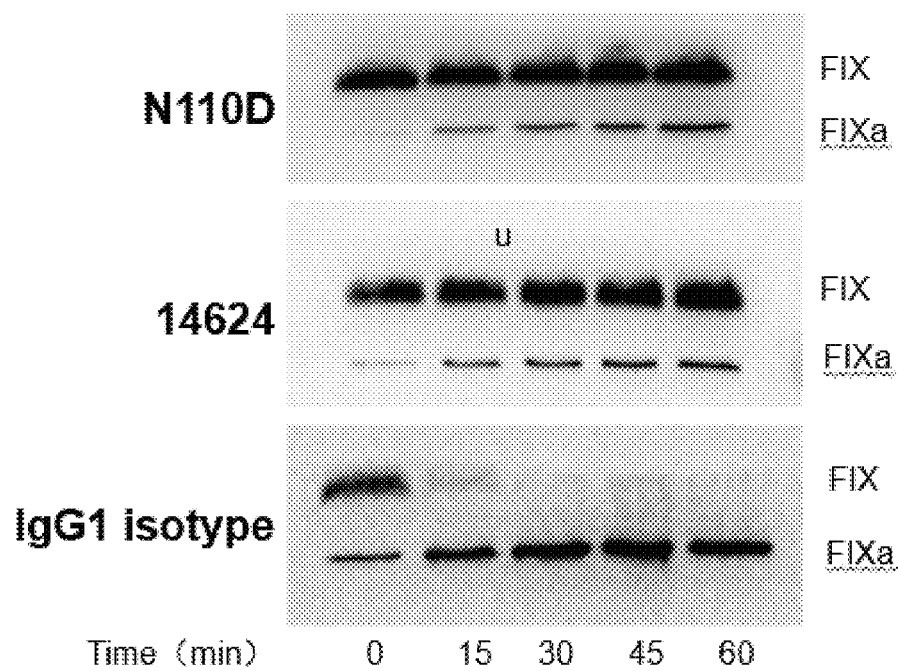
FIG. 7 illustrates the inhibitory effect of the monoclonal antibody 14624 on the FIX activation reaction mediated by human FXIa.

As shown in FIG. 7, compared with the IgG1 isotype control, both 14624 and the positive antibody N110D can inhibit the generation of FIXa mediated by FXI.

EXAMPLE 8 SPECIFIC INHIBITORY EFFECT OF THE ANTIBODY ON FXIa

In this example, the binding ability of coagulation factors PK, PKa, FXII, FXIIa, FIX, FIXa, FX, FXa, FVIIa, and Thrombin to antibodies at a series of diluted concentrations was analyzed using ELISA.

Figure 8:
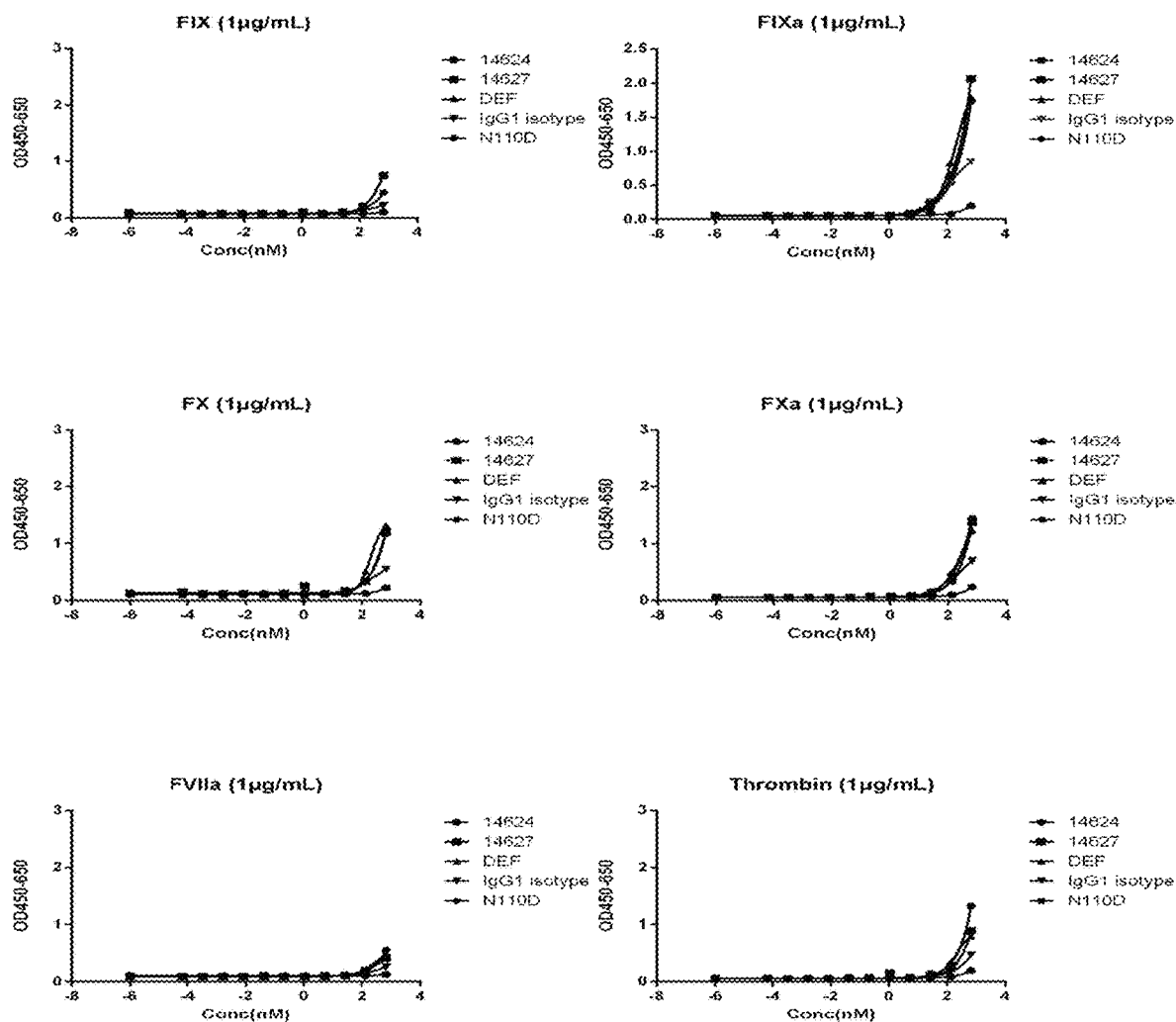
FIG. 8 illustrates curves of monoclonal antibodies 14624 and 14627 binding to antigen human PK, PKa, FXII, FXIIa, FIX, FIXa, FX, FXa, FVIIa and Thrombin.
Figure 9:
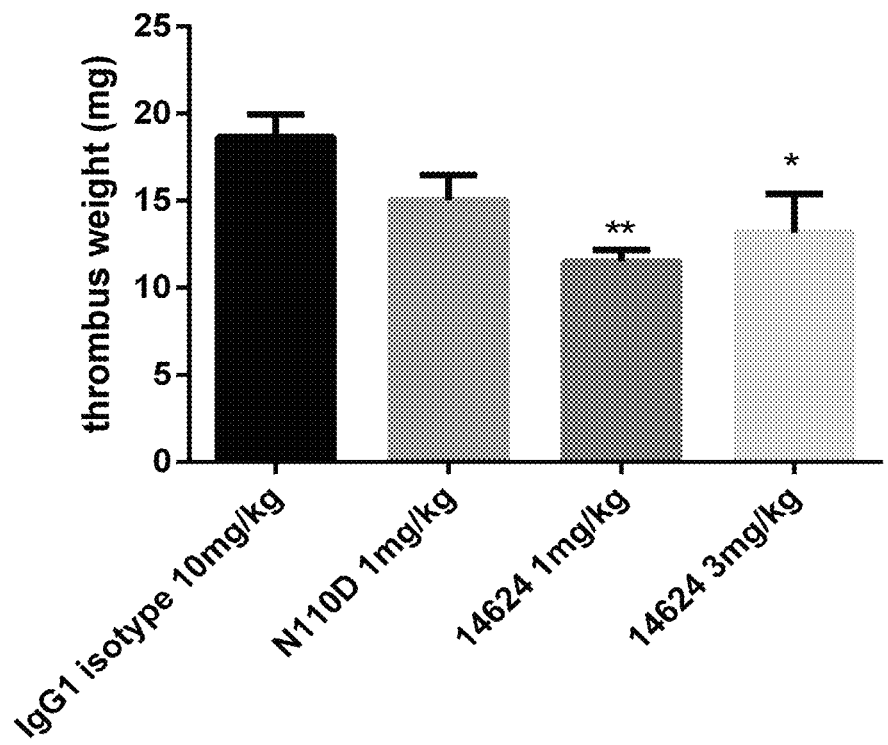
FIG. 9 illustrates the inhibitory effect of the monoclonal antibody 14624 on the weight of thrombus formed in arteriovenous shunt in New Zealand white rabbits.
Figure 10:
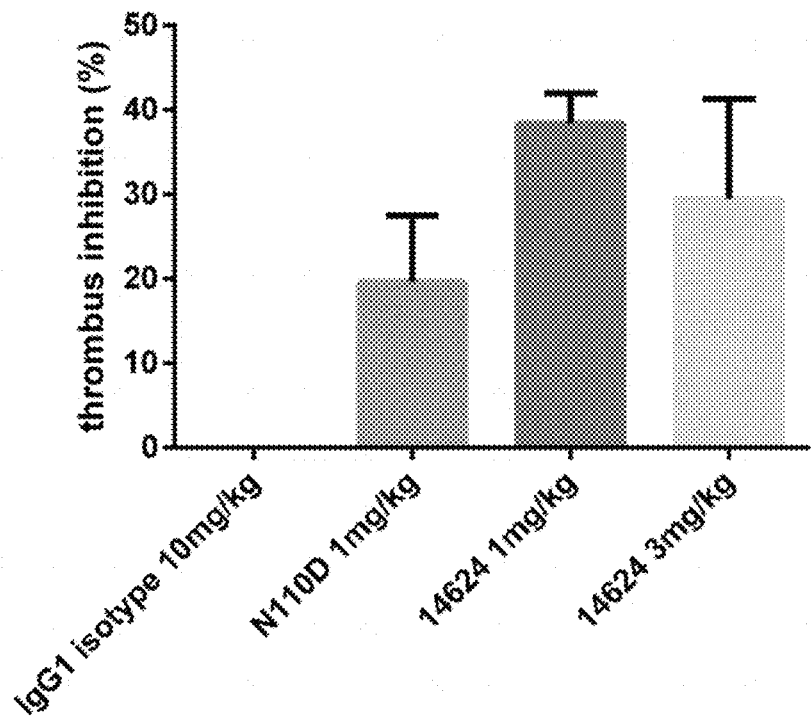
FIG. 10 illustrates the inhibitory effect of the monoclonal antibody 14624 on the formation of arteriovenous shunt thrombus in New Zealand white rabbits.
Figure 11A:
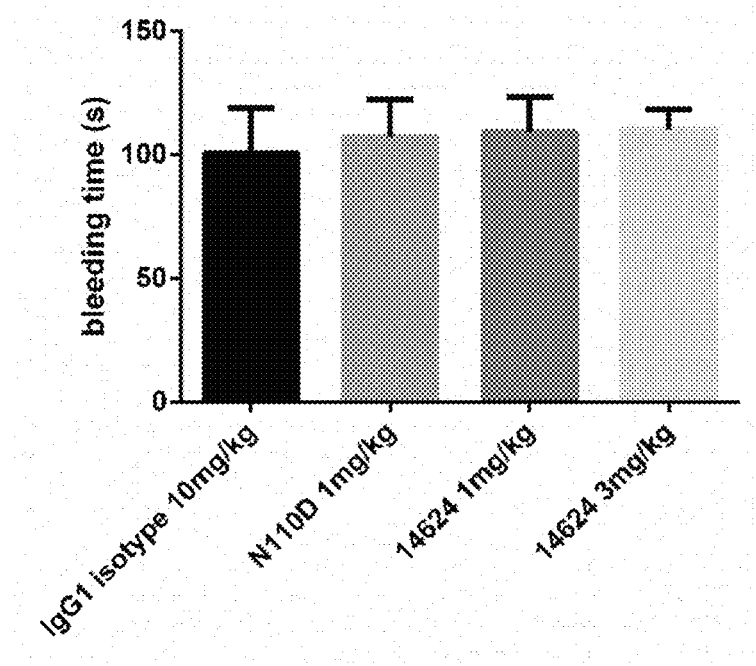
FIG. 11(A) illustrates the effect of the monoclonal antibody 14624 on the bleeding time in New Zealand white rabbits.
Figure 11B:
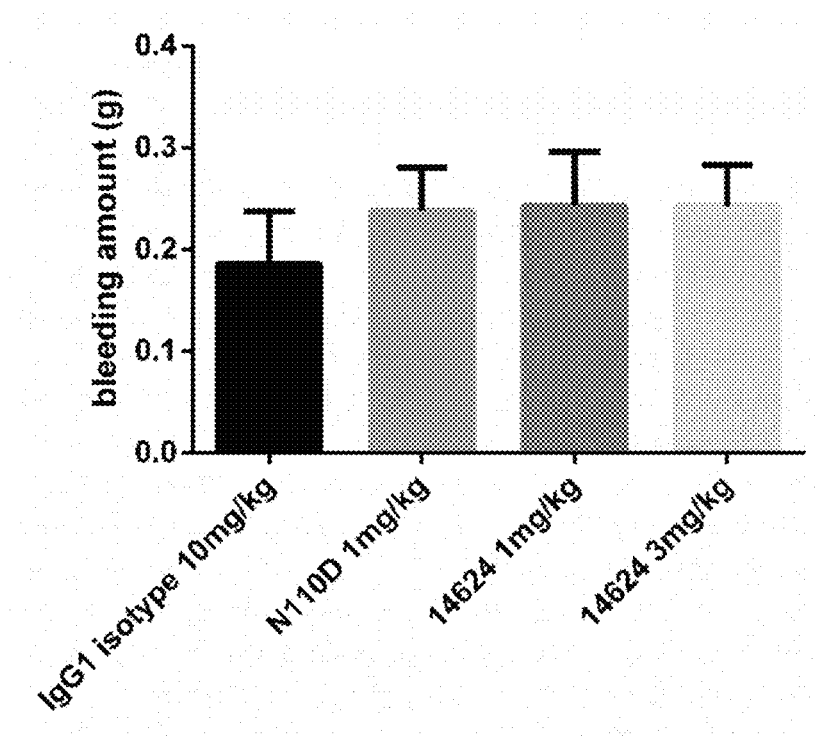
FIG. 11(B) illustrates the effect of the monoclonal antibody 14624 on the bleeding amount in New Zealand white rabbits.

As shown in FIG. 8, neither the antibodies to be detected nor the positive control antibody bound specifically to other coagulation factors in the intrinsic and extrinsic coagulation pathways.

EXAMPLE 9 EFFECT OF THE ANTIBODY ON THE FORMATION OF ARTERIOVENOUS BYPASS THROMBUS IN NEW ZEALAND RABBITS 30 male New Zealand rabbits were randomly divided into five groups according to their body weights, each with 6 rabbits. The doses of administration were as follows: 10 mg/kg IgG1 isotype in the normal saline as negative control group, 1 mg/kg N110D as the positive control group, 1 mg/kg antibody as the low-dose group, and 3 mg/kg antibody as the high-dose group, respectively. The route of administration was a single intravenous bolus into the ear margin vein.

Blood samples were collected in all animals before dosing (pre-perfusion) and at 30 min after dosing (post-perfusion) to detect Prothrombin time (PT), activated partial thromboplastin time (aPTT), and platelet count (PLT). After 2 min of the formation of the arteriovenous bypass blood flow in the neck of all New Zealand rabbits, a 3 mm incision was made at the same location on the ear margin vein, and the bleeding time and the bleeding amount were recorded.

At 30 min after dosing, the wet weight of the thrombus was recorded, and the inhibitory rate on the formation of thrombus was calculated.

The data were processed using the statistical software SPSS13.0, and the quantitative data were expressed as mean±standard error. The specific analysis process was as follows.

The equal variance was tested using Levene's. If there was an equal variance (P>0.05), statistical analysis was performed using the one-way ANOVA. If the ANOVA was statistically significant (P≤0.05), the comparative analysis was further performed using the LSD test (parametric method). If the variance was unequal (P≤0.05), the testing was performed by Kruskal-Wallis. If the Kruskal-Wallis test was statistically significant (P≤0.05), the two-two comparisons among the means were performed by Mann-Whitney method.

As shown in FIGS. 9, 10, 11(A) and 11(B), both the antibody low-dose and high-dose groups significantly inhibited arteriovenous shunt thrombus weight and thrombus formation (thrombus inhibition), but did not increase the bleeding time or the bleeding amount.

Figure 12:
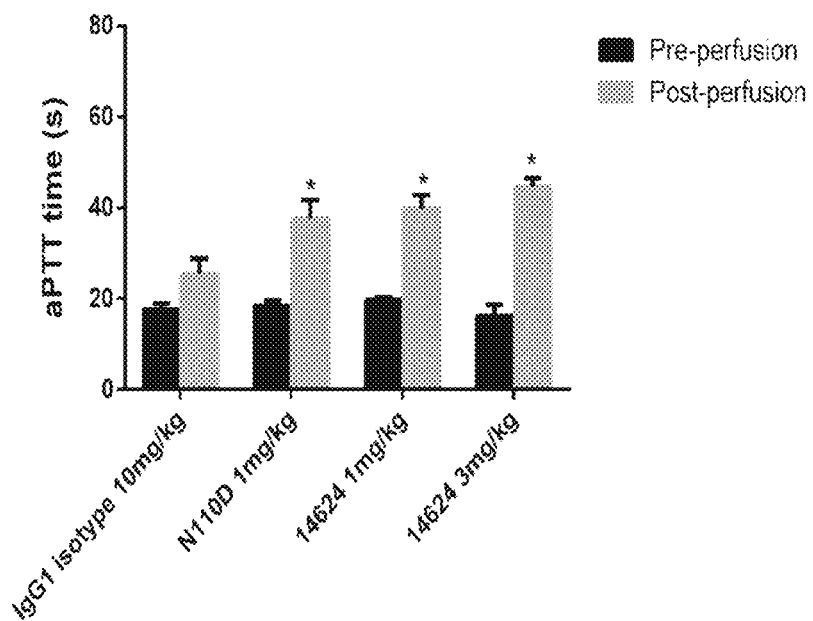
FIG. 12 illustrates the effect of the monoclonal antibody 14624 on activated partial thromboplastin time (aPTT) in New Zealand white rabbits.
Figure 13:
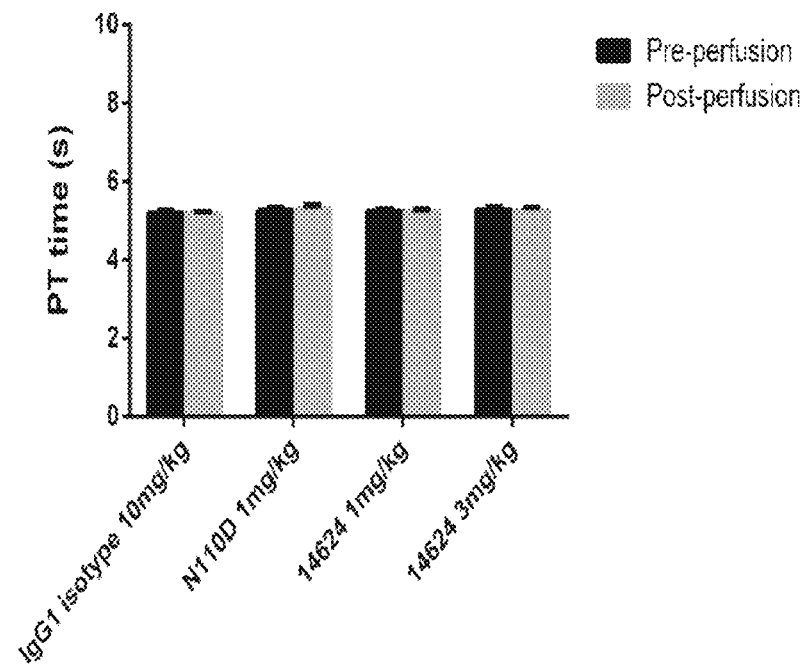
FIG. 13 illustrates the effect of the monoclonal antibody 14624 on prothrombin time (PT) in New Zealand white rabbits.
Figure 14:
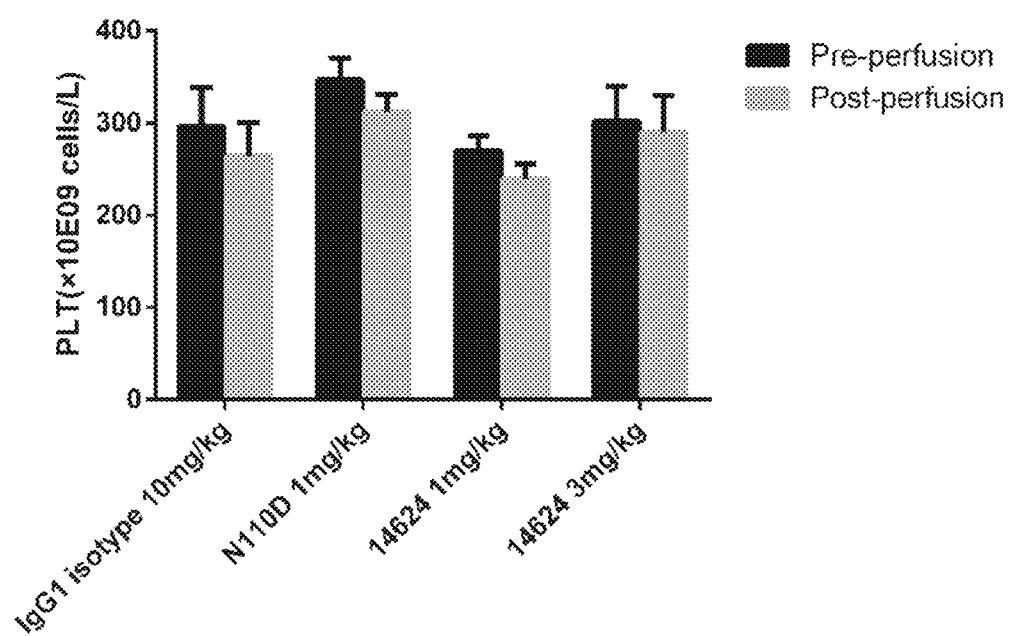
FIG. 14 illustrates the effect of the monoclonal antibody 14624 on the platelet count in New Zealand white rabbits.

As shown in FIGS. 12, 13 and 14, compared with the control groups, both the antibody low-dose and high-dose groups significantly increased the aPTT, but did not increase the PT or the platelet count.

In summary, the monoclonal antibody 14624 of the present application binds strongly to FXIa but not to FXI, and has a high affinity with FXIa; the monoclonal antibody 14624 increases aPTT without any significant effect on PT, and has the effect of inhibiting the intrinsic pathway of human coagulation without affecting the extrinsic pathway; such an antibody can inhibit the FXI-induced generation of FIXa, has the specific inhibitory effect on FXIa, and does not specifically bind to other coagulation factors in the intrinsic and extrinsic coagulation pathways; and the antibody can significantly inhibit the formation of arteriovenous shunt thrombus, and increase aPTT. Therefore, the antibody has the potential to become antithrombotic drugs.

The applicant has stated that although the detailed method of the present application is described through the examples described above, the present application is not limited to the detailed method described above, which means that implementation of the present application does not necessarily depend on the detailed method described above. It should be apparent to those skilled in the art that any improvements made to the present application, equivalent replacements of raw materials of the product of the present application, additions of adjuvant ingredients to the product of the present application, and selections of specific manners, etc., all fall within the protection scope and the disclosed scope of the present application.

What is claimed is:

1. An antigen-binding fragment of an anti-Factor XIa antibody, said antibody comprising heavy chain and light chain variable regions, wherein complementarity determining regions (CDRs) of said heavy chain variable region comprises amino acid sequences having SEQ ID NOs: 1, 2, and 3; and CDRs of said light chain variable region comprises amino acid sequences having SEQ ID NOs: 4, 5, and 6.

2. The antigen-binding fragment according to claim 1, wherein the CDRs of the heavy chain variable region comprises nucleic acid sequences having SEQ ID NOs: 7, 8 and 9; and the CDRs of the light chain variable region comprises nucleic acid sequences having SEQ ID NOs: 10, 11 and 12.

3. The antigen-binding fragment according to claim 1, wherein the heavy chain variable region comprises an amino acid sequence having SEQ ID NO: 13; and the light chain variable region comprises an amino acid sequence having SEQ ID NO: 14.

4. The antigen-binding fragment according to claim 3, wherein the heavy chain variable region comprises a nucleic acid sequence having SEQ ID NO: 15; and the light chain variable region comprises a nucleic acid sequence having SEQ ID NO: 16.

5. An anti-Factor XIa antibody, comprising the antigen-binding fragment according claim 1, wherein Factor XIa is the activated form of coagulation-factor XI.

6. The antibody according to claim 5, wherein the antibody further comprises any one or a combination of at least two of a human IgG1 constant region, a human IgG2 constant region, a human IgG3 constant region, or a human IgG4 constant region.

7. A nucleic acid molecule, comprising a DNA fragment encoding the antigen-binding fragment according to claim 1.

8. An expression vector, comprising the nucleic acid molecule according to claim 7.

9. The expression vector according to claim 8, wherein the expression vector comprises a pcDNA3.3 expression vector.

10. A host cell that is transfected with the nucleic acid molecule according to claim 7.

11. The host cell according to claim 10, wherein the host cell comprises a mammalian cell.

12. A preparation method of the antibody according to claim 5, comprising the following steps:
(1) ligating DNA fragments of a heavy chain variable region and a light chain variable region of an antibody into an expression vector, transferring the expression vector into a competent cell, culturing, and selecting a monoclonal cell for screening; and
(2) transferring the screened expression vector into a host cell, culturing, collecting a supernatant, and performing separation and purification to obtain the antibody.

13. A pharmaceutical composition, comprising the antibody according to claim 5.

14. A therapeutic agent that is ligated to the antibody according to claim 5.

15. A method for treating thrombus, comprising administering to a patient in need thereof an effective amount the antibody according to claim 5.

16. The host cell according to claim 11, wherein the host cell comprises a Chinese hamster ovary cell.

17. The pharmaceutical composition according to claim 13, wherein the pharmaceutical composition further comprises any one or a combination of at least two of a pharmaceutically acceptable carrier, excipient, or diluent.

18. The therapeutic agent according to claim 14, wherein the therapeutic agent further comprises any one or a combination of at least two of a pharmaceutically acceptable carrier, excipient, or diluent.

* * * * *

SEQUENCE LISTING

```
<160> NUMBER OF SEQ ID NOS: 16

<210> SEQ ID NO 1
<211> LENGTH: 5
<212> TYPE: PRT
<213> ORGANISM: Artificial sequence
<220> FEATURE:
<223> OTHER INFORMATION: CDR

<400> SEQUENCE: 1

Glu Leu Ser Met His
1               5

<210> SEQ ID NO 2
<211> LENGTH: 17
<212> TYPE: PRT
<213> ORGANISM: Artificial sequence
<220> FEATURE:
<223> OTHER INFORMATION: CDR

<400> SEQUENCE: 2
```

-continued

Gly Phe Asp Pro Glu Asp Gly Glu Thr Ile Tyr Ala Gln Lys Phe Gln
1               5                   10                  15

Gly

<210> SEQ ID NO 3
<211> LENGTH: 18
<212> TYPE: PRT
<213> ORGANISM: Artificial sequence
<220> FEATURE:
<223> OTHER INFORMATION: CDR

<400> SEQUENCE: 3

Asp Arg Pro Val Arg Gly Val Ile Pro Tyr Tyr Tyr Tyr Gly Met
1               5                   10                  15

Asp Val

<210> SEQ ID NO 4
<211> LENGTH: 13
<212> TYPE: PRT
<213> ORGANISM: Artificial sequence
<220> FEATURE:
<223> OTHER INFORMATION: CDR

<400> SEQUENCE: 4

Ser Gly Ser Arg Ser Asn Ile Gly Ser Arg Pro Val Asn
1               5                   10

<210> SEQ ID NO 5
<211> LENGTH: 7
<212> TYPE: PRT
<213> ORGANISM: Artificial sequence
<220> FEATURE:
<223> OTHER INFORMATION: CDR

<400> SEQUENCE: 5

Ile Asp His Gln Arg Pro Ser
1               5

<210> SEQ ID NO 6
<211> LENGTH: 11
<212> TYPE: PRT
<213> ORGANISM: Artificial sequence
<220> FEATURE:
<223> OTHER INFORMATION: CDR

<400> SEQUENCE: 6

Ala Ala Trp Asp Asp Ser Leu Asp Ala Tyr Val
1               5                   10

<210> SEQ ID NO 7
<211> LENGTH: 15
<212> TYPE: DNA
<213> ORGANISM: Artificial sequence
<220> FEATURE:
<223> OTHER INFORMATION: CDR

<400> SEQUENCE: 7
gaattatcca tgcac                                                    15

<210> SEQ ID NO 8
<211> LENGTH: 51
<212> TYPE: DNA
<213> ORGANISM: Artificial sequence
<220> FEATURE:
<223> OTHER INFORMATION: CDR

<400> SEQUENCE: 8
ggttttgatc ctgaagatgg tgaaacaatc tacgcacaga agttccaggg c          51

<210> SEQ ID NO 9
<211> LENGTH: 54
<212> TYPE: DNA
<213> ORGANISM: Artificial sequence
<220> FEATURE:
<223> OTHER INFORMATION: CDR

<400> SEQUENCE: 9
gatcggccgg ttcggggagt tattccttac tactactact acggtatgga cgtc       54

<210> SEQ ID NO 10
<211> LENGTH: 39
<212> TYPE: DNA
<213> ORGANISM: Artificial sequence
<220> FEATURE:
<223> OTHER INFORMATION: CDR

<400> SEQUENCE: 10
tctggaagcc gctccaacat cggaagtagg cctgtaaac                        39

<210> SEQ ID NO 11
<211> LENGTH: 21
<212> TYPE: DNA
<213> ORGANISM: Artificial sequence
<220> FEATURE:
<223> OTHER INFORMATION: CDR

<400> SEQUENCE: 11
attgatcatc agcggccctc a                                           21

<210> SEQ ID NO 12
<211> LENGTH: 33
<212> TYPE: DNA
<213> ORGANISM: Artificial sequence
<220> FEATURE:
<223> OTHER INFORMATION: CDR

<400> SEQUENCE: 12
gcagcatggg atgacagcct ggatgcttat gtc                              33

<210> SEQ ID NO 13
<211> LENGTH: 127
<212> TYPE: PRT
<213> ORGANISM: Artificial sequence
<220> FEATURE:
<223> OTHER INFORMATION: heavy chain variable region

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys

```
                    85                  90                  95
Ala Thr Asp Arg Pro Val Arg Gly Val Ile Pro Tyr Tyr Tyr Tyr
                   100                 105                 110
Gly Met Asp Val Trp Gly Gln Gly Thr Leu Val Thr Val Ser Ser
                   115                 120                 125
```

<210> SEQ ID NO 14
<211> LENGTH: 110
<212> TYPE: PRT
<213> ORGANISM: Artificial sequence
<220> FEATURE:
<223> OTHER INFORMATION: light chain variable region

<400> SEQUENCE: 14

```
Gln Ser Ala Leu Thr Gln Pro Pro Ser Ala Ser Gly Thr Pro Gly Gln
1               5                   10                  15

Thr Val Thr Ile Ser Cys Ser Gly Ser Arg Ser Asn Ile Gly Ser Arg
                20                  25                  30

Pro Val Asn Trp Tyr Gln His Leu Pro Gly Thr Ala Pro Lys Leu Leu
                35                  40                  45

Ile Tyr Ile Asp His Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Asp Asp Glu Ala Asp Tyr Tyr Cys Ala Ala Trp Asp Ser Leu
                    85                  90                  95

Asp Ala Tyr Val Phe Gly Thr Gly Thr Lys Val Thr Val Leu
                   100                 105                 110
```

<210> SEQ ID NO 15
<211> LENGTH: 381
<212> TYPE: DNA
<213> ORGANISM: Artificial sequence
<220> FEATURE:
<223> OTHER INFORMATION: heavy chain variable region

<400> SEQUENCE: 15

| | |
|---|---:|
| caggtccagc tggtacagtc tggggctgag gtgaagaagc ctggggcctc agtgaaggtc | 60 |
| tcctgcaagg tttccggata caccctcact gaattatcca tgcactgggt gcgacaggct | 120 |
| cctgaaaaag gcttgagtg gatgggaggt tttgatcctg aagatggtga acaatctac | 180 |
| gcacagaagt tccagggcag agtcaccatg accgaggaca tcctacaga cacagcctac | 240 |
| atggagctga gcagcctgag atctgaggac acggccgtgt attactgtgc aacagatcgg | 300 |
| ccggttcggg gagttattcc ttactactac tactacggta tggacgtctg ggccaaggg | 360 |
| accctggtca ccgtctcgag c | 381 |

<210> SEQ ID NO 16
<211> LENGTH: 330
<212> TYPE: DNA
<213> ORGANISM: Artificial sequence
<220> FEATURE:
<223> OTHER INFORMATION: light chain variable region

<400> SEQUENCE: 16

| | |
|---|---:|
| cagtctgccc tgactcagcc accctcagcg tctgggaccc ccgggcagac ggtcaccatc | 60 |
| tcttgctctg gaagccgctc caacatcgga agtaggcctg taaactggta ccagcacctc | 120 |
| ccaggaacgg ccccaaact cctcatctat attgatcatc agcggccctc aggggtccct | 180 |

```
gaccgattct ctggctccaa gtctggcacc tcagcctccc tggccatcag tgggctccag      240
tctgacgatg aggctgatta ttactgtgca gcatgggatg acagcctgga tgcttatgtc      300
ttcggaactg ggaccaaggt caccgtccta                                       330
```